United States Patent
Oralkan et al.

(10) Patent No.: US 8,852,104 B2
(45) Date of Patent: Oct. 7, 2014

(54) METHOD AND APPARATUS FOR ULTRASOUND ASSISTED LOCAL DELIVERY OF DRUGS AND BIOMARKERS

(75) Inventors: Omer Oralkan, Santa Clara, CA (US); Butrus T. Khuri-Yakub, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 664 days.

(21) Appl. No.: 12/798,982

(22) Filed: Apr. 14, 2010

(65) Prior Publication Data

US 2010/0268152 A1    Oct. 21, 2010

Related U.S. Application Data

(60) Provisional application No. 61/212,833, filed on Apr. 15, 2009.

(51) Int. Cl.
*A61B 5/05* (2006.01)
*A61B 5/00* (2006.01)
*A61M 37/00* (2006.01)

(52) U.S. Cl.
CPC .......... *A61B 5/0095* (2013.01); *A61M 37/0092* (2013.01); *A61B 5/0084* (2013.01)
USPC .......................................... 600/439; 600/427

(58) Field of Classification Search
USPC ......... 600/439, 463, 476, 427, 458, 437, 473;
607/89; 73/644, 632, 642, 861.26, 599;
359/385; 331/18; 540/460; 604/22;
601/2
See application file for complete search history.

(56) References Cited

U.S. PATENT DOCUMENTS

| | | | |
|---|---|---|---|
| 4,659,956 A * | 4/1987 | Trzaskos et al. | 310/335 |
| 4,697,195 A | 9/1987 | Quate et al. | |
| 5,307,816 A * | 5/1994 | Hashimoto et al. | 600/439 |
| 6,070,468 A * | 6/2000 | Degertekin et al. | 73/644 |
| 6,428,532 B1 * | 8/2002 | Doukas et al. | 606/9 |
| 2002/0082666 A1* | 6/2002 | Babaev | 607/89 |
| 2003/0199765 A1* | 10/2003 | Stetten et al. | 600/439 |
| 2004/0085858 A1* | 5/2004 | Khuri-Yakub et al. | 367/181 |
| 2006/0013454 A1* | 1/2006 | Flewelling et al. | 382/128 |
| 2010/0063403 A1 | 3/2010 | Mendelson | |
| 2010/0069797 A1 | 3/2010 | Cain et al. | |
| 2010/0069844 A1 | 3/2010 | Bonner et al. | |

OTHER PUBLICATIONS

Hyejun Ra et al (Two-Dimenional MEMS Scanner for Dual-Axes Confocal Microscopy form Journal of Microelectromechanical system), Aug. 4, 2007, vol. 16. pp. 969-975.*

* cited by examiner

*Primary Examiner* — Long V. Le
*Assistant Examiner* — Lawrence Laryea
(74) *Attorney, Agent, or Firm* — Lumen Patent Firm

(57) ABSTRACT

The current invention provides an ultrasound-assisted delivery device, that includes a focused ultrasound transducer having an ultrasound focal point, a real-time imaging device having an imaging focal point, and a therapeutic delivery device, where the transducer and the imaging device are integrated with the delivery device, and the ultrasound focal point coincides with the imaging focal point, where the delivery device and transducer are disposed to provide an unobstructed imaging path for the real-time imaging device. The invention further includes a scanning optical or laser beam having a focal point disposed to sweep across the target, where the delivery device is disposed to deliver an optical contrast material to the target, and the scanning focal point coincides with the ultrasound and imaging focal points, where the target or the optical contrast material react to the scanning beam to generate at least one interface signal.

20 Claims, 5 Drawing Sheets

METHOD AND APPARATUS FOR ULTRASOUND ASSISTED LOCAL DELIVERY OF DRUGS AND BIOMARKERS

CROSS-REFERENCE TO RELATED APPLICATIONS

This application claims priority from U.S. Provisional Patent Application 61/212,833 filed Apr. 15, 2009, which is incorporated herein by reference.

STATEMENT REGARDING FEDERALLY SPONSORED RESEARCH OR DEVELOPMENT

This invention was made with Government support under contract CA136465 awarded by National Institutes of Health (NIH). The Government has certain rights in this invention.

FIELD OF THE INVENTION

The present invention relates generally to medical devices and techniques. More specifically, it relates to devices and techniques for the local delivery of drugs or biomarkers using ultrasound.

BACKGROUND OF THE INVENTION

Ultrasound has been widely used in medical applications for both diagnostic and therapeutic purposes. Diagnostic imaging is probably the most common application of ultrasound in medicine. The exposure intensity levels for diagnostic ultrasound are below 0.5 W/cm$^2$. At the other end of the spectrum, high intensity focused ultrasound (>1000 W/cm$^2$) is used to destroy tissue to treat cancers and other abnormalities such as arrhythmias in the heart. Ultrasound intensities in the mid-range (e.g., 0.5-3 W/cm$^2$) are used for other therapeutic applications such as in physical therapy or to enhance drug delivery.

A first report on the use of ultrasound to enhance drug delivery used ultrasound to drive hydrocortisone ointment into inflamed tissues for treating poly arthritis. The ultrasound-assisted delivery of drug molecules across the percutaneous barrier to a target area is called 'phonophoresis'. This technique has been used for several drugs. In addition, ultrasound has also been shown to enhance the effects of several therapeutic drug classes, including chemotherapeutic, thrombolytic, and gene-based drugs. Ultrasound enhances drug delivery through thermal mechanisms as well as non-thermal mechanisms such as cavitation, radiation pressure, and acoustic microstreaming. In some cases, these mechanisms act at the tissue level and in some cases at the cellular level. Transient permeabilization of the cell membrane, which may occur during cavitation, leads to uptake of molecules into the cell. This phenomenon, called 'sonoporation', has been confirmed by many studies, also for gene transfer. Sonoporation is often conducted with the help of microbubbles, which are originally developed as contrast agents for diagnostic ultrasound imaging. Local delivery of drugs is important for localized treatment of anomalies such as tumors without harming the surrounding healthy tissue. What is needed is a device and method to improve the efficiency of the local treatment and to monitor localized drug delivery of the treatment spot.

SUMMARY OF THE INVENTION

The current invention provides an ultrasound-assisted delivery device, that includes a focused ultrasound transducer having an ultrasound focal point, a real-time imaging device having an imaging focal point, and a therapeutic delivery device, where the focused ultrasound transducer and the real-time imaging device are integrated with the therapeutic delivery device, and the ultrasound focal point coincides with the imaging focal point, where the therapeutic delivery device and the focused ultrasound transducer are disposed to provide an unobstructed imaging path for the real-time imaging device.

According to one aspect of the invention, the focused ultrasound transducer includes piezoelectric material.

In another aspect of the invention, the therapeutic delivery device includes an endoscope, a catheter providing internal delivery, or an external device providing skin delivery.

In a further aspect, the real-time imaging device includes a dual-axis confocal microscope, where the focused ultrasound transducer is disposed on a backside of an imaging mirror in the dual-axis confocal microscope.

According to one aspect of the invention, the focused ultrasonic transducer comprises a circular pattern of electrodes. Here, the focused ultrasonic transducer provides a radial pattern of surface acoustic waves, or Lamb waves on a surface of a target for delivery, where the radial pattern of surface acoustic waves or the Lamb waves undergo a mode conversion to longitudinal waves to provide a focused ultrasonic beam.

In another aspect of the invention, the focused ultrasonic transducer is an interdigital ultrasonic transducer having a piezoelectric material, a first interdigital electrode, a second interdigital electrode and a metal layer, where the first interdigital electrode is disposed on a back side of an imaging mirror in the real-time imaging device and the second interdigital electrode is disposed proximal to the first electrode, where the piezoelectric material is disposed on the first electrode and on the second electrode, and the metal layer is disposed on the piezoelectric material. Here, the spacing between the first electrode and the second electrode is about one quarter wavelength of a leaky Rayleigh wave.

In another aspect of the invention, the focused ultrasonic transducer is an edge bonded ultrasonic transducer that includes a piezoelectric material, a first segmented cylindrical electrode and a second segmented cylindrical electrode, where the first segmented cylindrical electrode is disposed about an edge of an imaging mirror in the real-time imaging device, where the piezoelectric material is disposed on the first segmented electrode, and the second segmented cylindrical electrode is disposed on the piezoelectric material, where the piezoelectric material is electrically driven to generate surface acoustic waves along a back surface of the imaging mirror.

In yet another aspect of the invention, the focused ultrasonic transducer includes a spherically focused ultrasonic transducer having a parabolic first electrode, a piezoelectric material disposed on the parabolic first electrode and a second electrode disposed on the piezoelectric material.

According to one aspect of the invention, the ultrasound assisted delivery device further includes a laser beam having a laser beam focal point, where the therapeutic delivery device is disposed to deliver an optical contrast material to the target, and the laser beam focal point coincides with the ultrasound focal point and with the imaging focal point, and the laser beam focal point is disposed to sweep across the target, where the target or the optical contrast material absorbs energy from the laser beam focal point to generate at least one interface signal. Here, the focused ultrasound transducer can include a bi-static transducer or a mono-static transducer, where the bi-static transducer is disposed to transmit and to receive acoustic signals, and the mono-static transducer is disposed to receive the acoustic signals. Further, the at least one interface signal can include i) a fluorescence signal formed by the contrast material absorbing energy from the laser focal point, ii) interface acoustic waves formed by endogenous absorption in the target, iii) interface acoustic waves formed by exogenous absorbing contrast agents in the target, i) and ii), ii and iii), or i) and iii), where the fluorescence signal is received by the real-time imaging device, and the interface acoustic waves are laterally propagating waves that are received by the transducer, and the transducer is disposed to operate in a receiving mode. According to another aspect the laser light source can include i) a pulsed laser light source. ii) a continuous wave laser light source, or i) and ii). In a further aspect, the transducer can be switched from a receive mode to a transmit mode, where when in the receive mode the transducer is disposed for imaging the target and when in the transmit mode the transducer is disposed for treating the target. In another aspect, an output power of the transducer is adjustable. In a further aspect, the optical contrast material can include lipid or protein-based nanoparticles, metallic nanoparticles, or fluorescent dye.

In another aspect, the invention is an ultrasound assisted delivery device including an imaging device having an imaging focal point, a therapy delivery device having a delivery focus point, and a transducer that includes capacitive micromachined ultrasonic transducers (CMUT) arranged in an interdigital pattern to provide interface modes, where the interface modes are disposed to focus at a center of the transducer and disposed to coincide with the imaging focal point and the delivery focus point.

According to one aspect, the transducer includes a piezoelectric micromachined ultrasonic transducer (PMUT) disposed to generate the interface modes.

In a further aspect, the transducer includes a magnetic actuated micromachined ultrasonic transducer disposed to generate the interface modes.

DETAILED DESCRIPTION

One aspect of the current invention provides an ultrasound-assisted delivery device that includes a focused ultrasound transducer having an ultrasound focal point, a real-time imaging device having an imaging focal point, and a therapeutic delivery device, where the focused ultrasound transducer and the real-time imaging device are integrated with the therapeutic delivery device, and the ultrasound focal point coincides with the imaging focal point, where the therapeutic delivery device and the focused ultrasound transducer are disposed to provide an unobstructed imaging path for the real-time imaging device.

According to one aspect of the invention, a focused ultrasound transducer is provided that is small (e.g., less than 5 mm in diameter) and is integrated with imaging devices (e.g., in endoscopes and catheters). The transducer is disposed to launch surface acoustic waves (SAW) into the tissue. Mode conversion to longitudinal waves results in an ultrasound beam focused at the desired location. According to the invention novel apparatuses are provided to assist the local delivery of drugs or biomarkers by using ultrasound and/or lasers.

According to another aspect, the current invention can be implemented in a very tight space without interfering with the light path, and therefore integrates ideally with intracavital imaging tools such as endoscopes or catheter-based devices.

According to one aspect of the current invention, the efficiency of the local treatment can be monitored when localized drug delivery is combined with real-time imaging of the treatment spot (also referred to as a target). The current invention provides focused ultrasound transducers in a tight space (e.g., <5 mm) that are integrated with imaging devices and used an endoscope, a catheter providing internal delivery, or an external device providing skin delivery.

One embodiment of the current invention provides an unobstructed or unaltered light path for optical imaging and laser scanning, so as to not interfere with the imaging device or beam path. According to the invention, the therapeutic device fits in a small area, and the construction process of the therapeutic device is compatible with the imaging device. The current invention provides a minimum number of electrical connections, for example 3-connections, and is operable in the imaging field of the imaging device to enable monitoring drug delivery in real time.

Figures 1, 2:
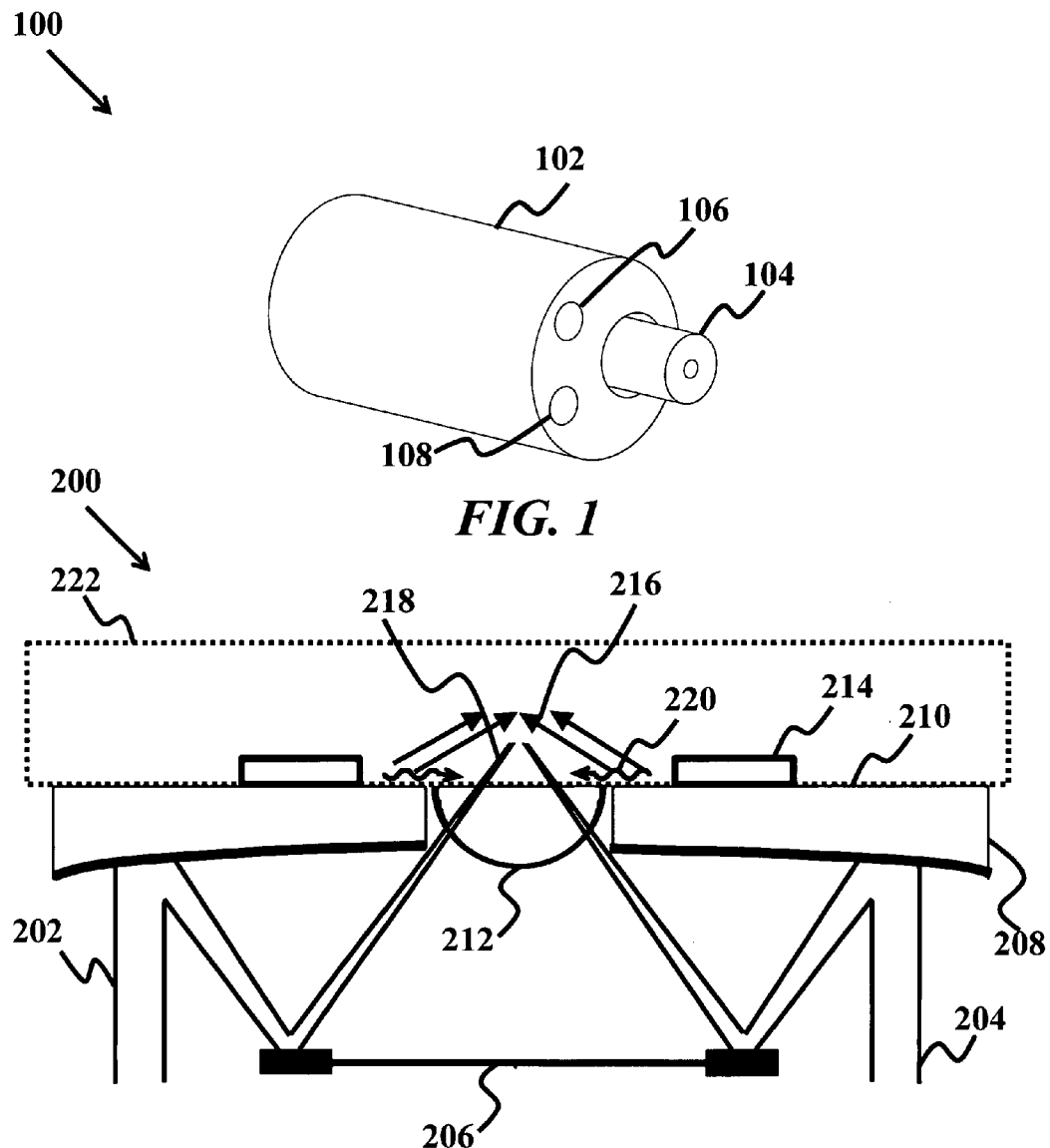
FIG. 1 shows a perspective view of an integration of delivery assisting devices with a dual-axes confocal microscope used in an endoscopic channel according to one aspect of the current invention.
FIG. 2 shows a planar schematic view of a focused ultrasound transducer disposed on the backside of a parabolic mirror utilized in the microscope, according to one aspect of the current invention.

In one aspect, the invention provides integration of delivery assisting devices 100 with a dual-axes confocal microscope used in an endoscopic channel as shown in FIG. 1. As shown, an endoscope tube 102 has an imaging device 104 with a front side disposed for incorporating a therapeutic delivery assisting device, and at least one imaging modality port 106 and at least one delivery port 108 for providing materials such as biomarkers or therapeutic agents.

FIG. 2 shows miniature dual-axis confocal scan head optics 200 for integrating to the front side of the imaging device 104. Further shown is a collimated illumination beam 202, a collimated collection beam 204, a microelectromechanical (MEMS) 2-D scanner 206, a parabolic reflecting surface 208 having a backside surface 210 and an index-matching hemisphere (or focus/collection optic) 212. Further, the current invention uses at least one focused ultrasound transducer 214 disposed on the backside 210 of a parabolic mirror 208 utilized in the microscope 104. In this example, the backside 210 of the mirror 208 is shown as a flat surface, circular in shape with a 5-mm diameter and a 2-mm opening in the middle for illumination and collection beams 202/204 to pass through. The ultrasound transducer 214 fits within the mirror area, and the construction process is compatible with the rest of the fixture, where a minimum number of electrical connections are used. The acoustic focus 216 is disposed to coincide with the optical focus 218, for example about 0.3 mm away from the mirror backside 210 surface, so that the ultrasound enhanced delivery process can be monitored using the microscope 104 in real time. The current invention can also be used with other kinds of similar imaging devices.

According to another aspect of the invention, the transducers launch surface acoustic waves (SAW) 220 on the surface that is in contact with the tissue 222 and then take advantage of mode conversion to longitudinal waves to obtain a focused ultrasound beam 216 at the desired location. The waves 220 propagate in the radial direction inwardly and outwardly. The acoustic energy is mode-convert into longitudinal waves 220 in the medium and leak into the medium in contact at a predetermined angle (by the Snell's law). Due to the circular symmetry of the structure, the waves 220 propagate longitudinally in the tissue 222 and focus 216 at the center. Thus, an elongated focal spot 216 starts from the surface of the transducer 214 and extends into the medium 222. The circular symmetry and the discontinuity at the edges help to direct the outwardly traveling waves 216 back toward the center to increase the efficiency of the transducer 214. According to the invention, there are different ways of exciting SAWs on a non-piezoelectric material. In one aspect, the transducer 214 is unidirectional, meaning that waves 216 will only be propagated inward from the transducer 214 and hence all the input energy goes towards the focus 216. According to the current invention, two different types of transducers 214 can be used to excite SAWs that include an interdigital transducer (see FIGS. 3(a)-3(c)) and an edge-bonded transducer (see FIGS. 4(a)-4(c)).

Figure 3:
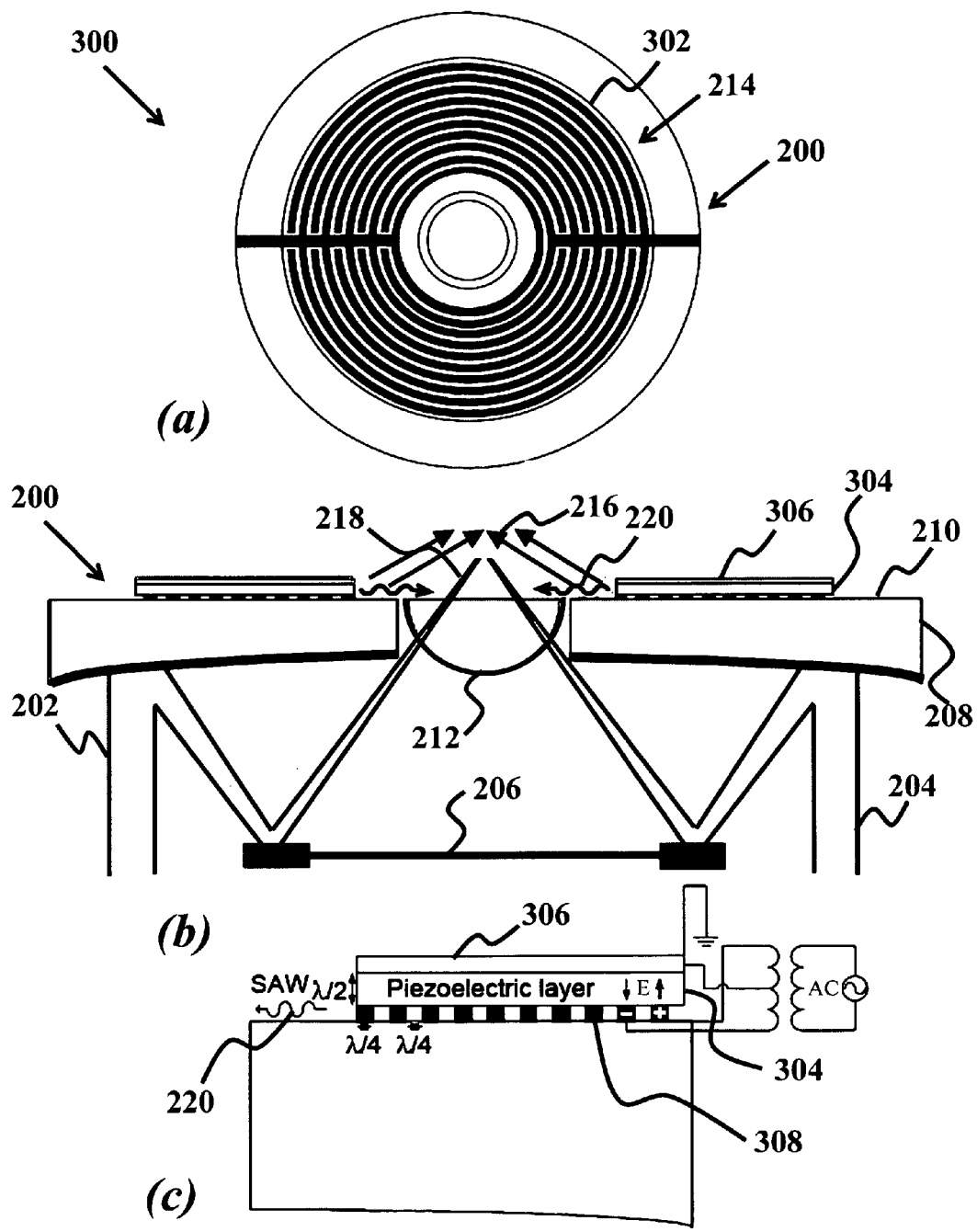
FIG. 3(a)-3(c) show a top view and planar schematic views of an integrated delivery assisting device having an interdigital transducer (IDT) for providing SAW excitation disposed on an imaging device, according to one aspect of the current invention.

In another aspect of the invention, the focused ultrasonic transducer is an interdigital ultrasonic transducer having a piezoelectric material, a first interdigital electrode, a second interdigital electrode and a metal layer, where the first interdigital electrode is disposed on a back side of an imaging mirror in the real-time imaging device and the second interdigital electrode is disposed proximal to the first electrode, where the piezoelectric material is disposed on the first electrode and on the second electrode, and the metal layer is disposed on the piezoelectric material. Here, the spacing between the first electrode and the second electrode is about one quarter wavelength of a leaky Rayleigh wave. FIG. 3(a)-3(c) show an integrated device 300 having an interdigital transducer 214 (IDT) for providing SAW excitation disposed on an imaging device 200, where FIG. 3(a) shows a top view of the IDT electrode pattern 302. The IDT 214 is disposed on backside 210 of the mirror 208. As shown, a thin layer of piezoelectric material 304 is placed on the non-piezoelectric substrate, in this example it is placed on the mirror backside 210. A metal film 306 can be optionally deposited on the opposite side. As a result, there are four possible configurations to implement IDTs 214. The use of a metal film 306 opposite to the IDT 214 is advantageous because it serves to concentrate the electric field in the piezoelectric material 304, which in turn increases the transducer impedance and coupling to the acoustic wave 220. In one aspect, the IDT electrodes 308 are placed directly on the backside 210 of the parabolic mirror 208. Then a piezoelectric material 304 is placed on top of the electrodes 308 with good acoustical contact and the metal film 306 is deposited on the opposite surface of the piezoelectric layer 304. Further, the transducers can be capacitive micromachined ultrasonic transducers (CMUT) arranged in an interdigital pattern to provide interface modes, where the interface modes are disposed to focus at a center of the transducer and disposed to coincide with the imaging focal point and the delivery focus point.

Deposited materials such as ZnO, AlN, LiNbO$_3$, BGO, LiTaO$_3$, PZT, or ceramics such as PZT can be used as the piezoelectric material. The electrode 308 width and spacing are a quarter of the wavelength of the leaky Rayleigh wave and the thickness of the piezoelectric material is one half of the wavelength of the leaky Rayleigh wave. For example, the SAW velocity on ST-X quartz is about 3000 m/s. At 10 MHz the wavelength is 0.3 mm. 4 circular IDT pairs can fit on the available area as shown in FIGS. 3(a)-3(c). Only three electrical connections, two IDT electrodes and one ground, are required to excite this transducer as shown in FIG. 3(c). With this type of transducer 214 implemented in a "uni-directional configuration", the unidirectional IDT uses three electrodes with phase shifts to have the wave propagate in one direction only, in this case towards the center so that there is no loss of 50% of the energy which would otherwise propagate away from the center. The three sets of fingers are used and appropriate phase-shifts to coherently add the excited waves towards the center of the rings, while they coherently subtract and cancel all energy excited in the outwards direction.

Figure 4:
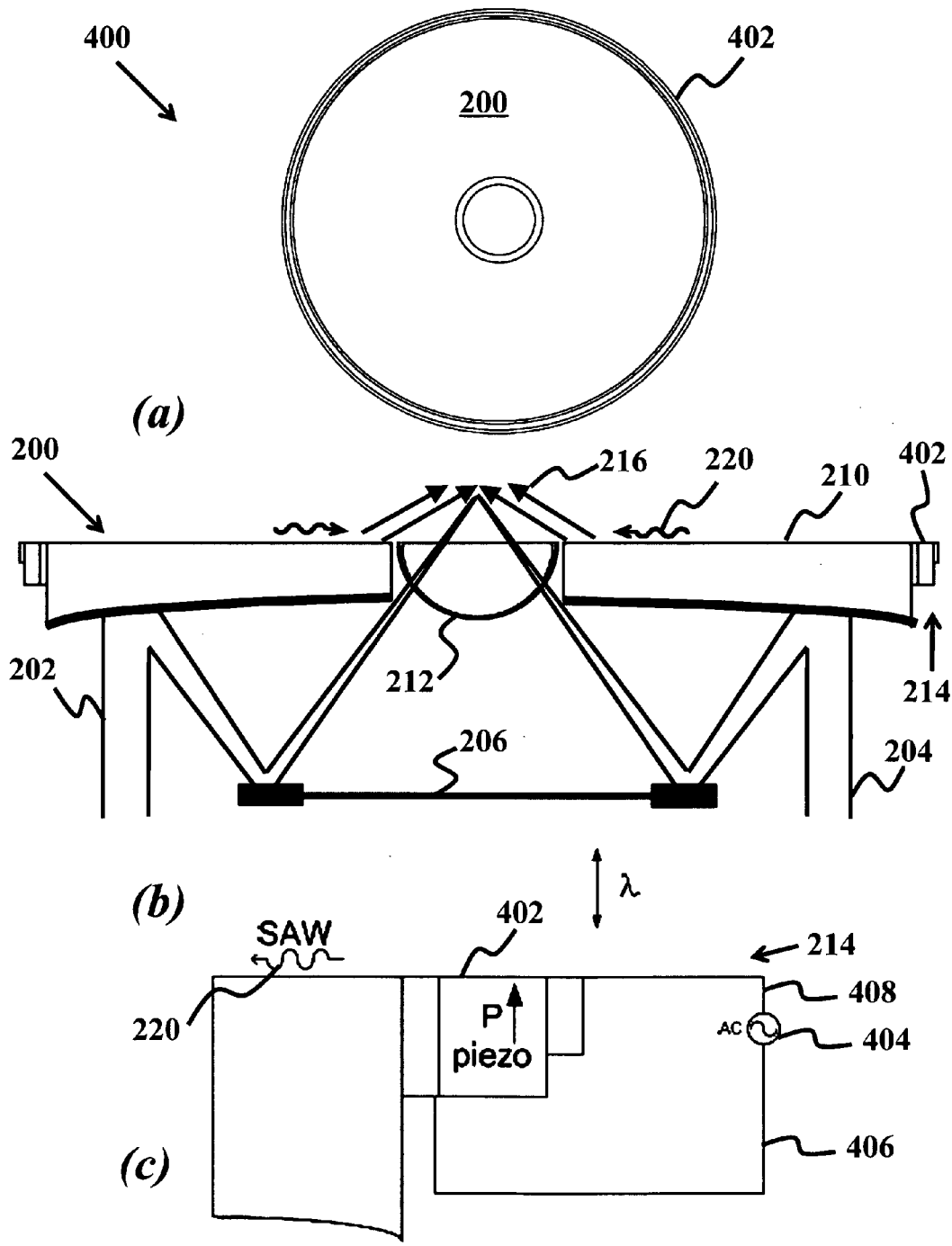
FIGS. 4(a)-4(c) show a top view and planar schematic views of an integrated delivery assisting device having edge-bonded transducer (EBT) based SAW excitation disposed on an imaging device, according to one aspect of the current invention.

FIGS. 4(a)-4(c) show an integrated delivery assisting device having edge-bonded transducer (EBT) based SAW excitation 400 disposed on an imaging device 200, according to the current invention. As shown, edge-bonded transducer 214 (EBT) based SAW excitation is used, where EBTs 214 have a higher efficiency and larger bandwidth than an IDTs 214. The current invention uses a piezoelectric hollow cylinder 402 (cut into two pieces) that is bonded around the parabolic mirror 208 as shown in FIGS. 4(a)-4(c). The transducer 214 is bonded to the face normal to the propagation direction of SAW 220. The input electrical signal 404 is applied between a ground electrode 406 and an outer electrode 408, where the transducer 214 is disposed near the edge of the mirror 208 shown in FIGS. 4(a)-4(c). The piezoelectric hollow cylinder material 404 is poled so as to generate a transverse displacement normal to the surface of the piezoelectric hollow cylinder 402 to excite Rayleigh waves. The mode conversion and focusing is similar to the IDT example.

Figure 5:
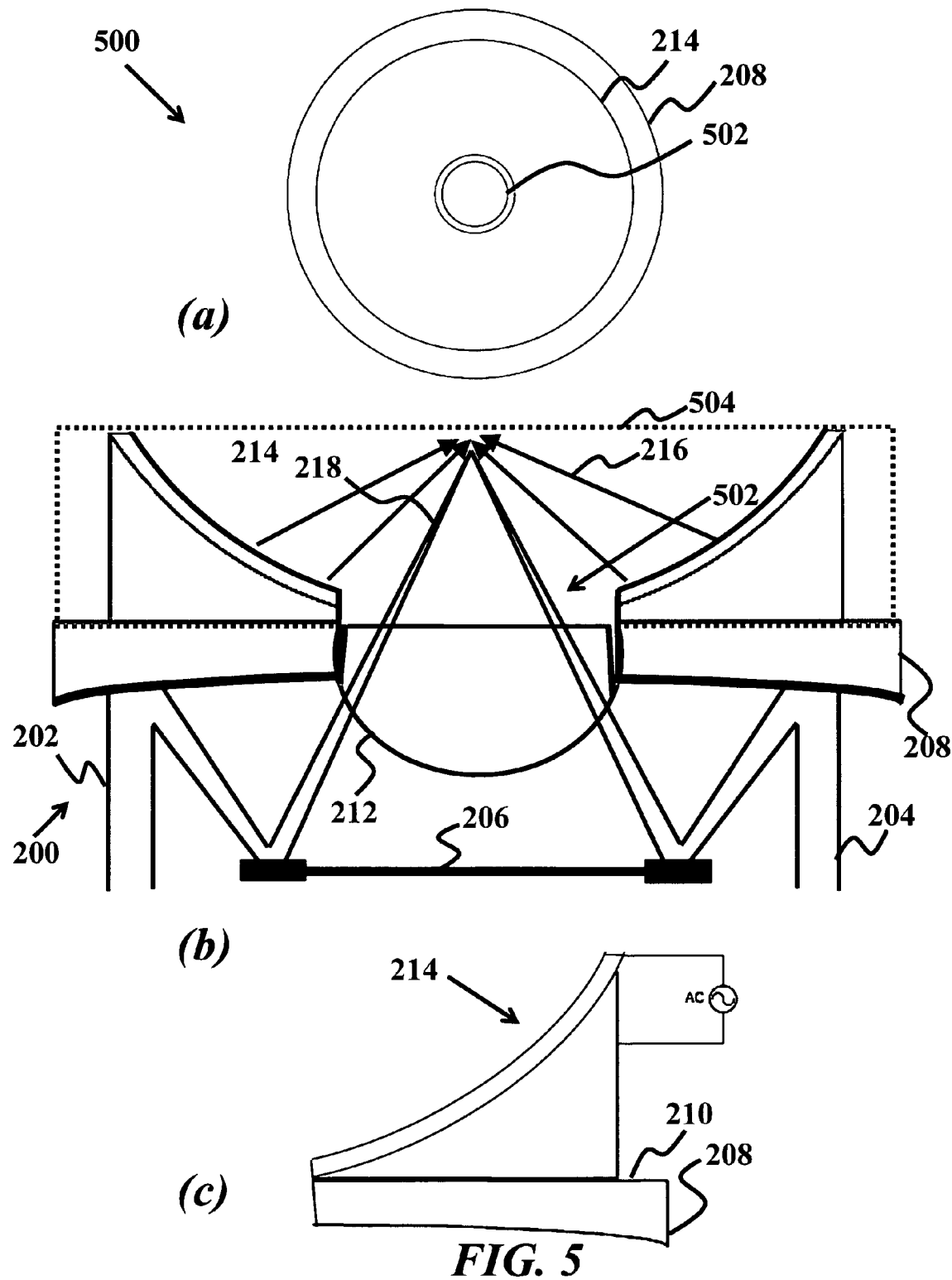
FIGS. 5(a)-5(c) show a top view and planar schematic views of an integrated delivery assisting device having spherically focused transducer disposed on an imaging device, according to one aspect of the current invention.

In yet another aspect of the invention, the focused ultrasonic transducer includes a spherically focused ultrasonic transducer having a parabolic first electrode, a piezoelectric material disposed on the parabolic first electrode and a second electrode disposed on the piezoelectric material. FIGS. 5(a)-5(c) show an integrated delivery assisting device having spherically focused transducer 500 disposed on an imaging device 200, according to the current invention. As shown, a spherically focused transducer 214 is adapted by introducing an opening 502 in the center of the transducer 214. Because the non-planar structure of the spherically focused transducers 214 makes the direct contact with tissue 222 difficult, an acoustic coupling medium 504 is provided. Also the acoustic focal point 216 is further away from the surface. So, the imaging device is disposed to have a deep focal point 218 to allow the real-time monitoring.

According to one aspect of the invention, the ultrasound assisted delivery device of further includes a laser beam having a laser beam focal point, where the therapeutic delivery device is disposed to deliver an optical contrast material to the target and the laser beam focal point coincides with the ultrasound focal point and with the imaging focal point, and the laser beam focal point is disposed to sweep across the target, where the target or the optical contrast material absorbs energy from the laser beam focal point to generate at least one interface signal. Here, the focused ultrasound transducer can include a bi-static transducer or a mono-static transducer, where the bi-static transducer is disposed to transmit and to receive acoustic signals, and the mono-static transducer is disposed to receive the acoustic signals. Further, the interface signal can include a fluorescence signal formed by the contrast material absorbing energy from the laser focal point, interface acoustic waves formed by endogenous absorption in the target, interface acoustic waves formed by exogenous absorbing contrast agents in the target or any combination of these signals, where the fluorescence signal is received by the real-time imaging device, and the interface acoustic waves are laterally propagating waves that are received by the transducer, and the transducer is disposed to operate in a receiving mode. The laser light source can include a pulsed laser light source and/or a continuous wave laser light source. In a further aspect, the transducer can be switched from a receive mode to a transmit mode, where when in the receive mode the transducer is disposed for imaging the target and when in the transmit mode the transducer is disposed for treating the target. In another aspect, an output power of the transducer is adjustable. In a further aspect, the optical contrast material can include lipid and protein-based nanoparticles, metallic nanoparticles, or fluorescent dye. For photo-acoustic imaging, the IDT 214 is used to receive energy. Using the IDT 214 in receive mode, the described transducer is combined with a scanning optical beam, which can be provided by the microscope or by a laser, enables photoacoustic imaging with optical resolution. The acoustic focal spot is typically larger than the optical focal spot, where the acoustic transducer is disposed to "listen" to the signals coming from its focal spot 216 and the optical beam 202 is scanned in this same region. When the optical spot 218 hits an absorbing target 222 a photoacoustic signal is generated and picked up by the acoustic transducer 214. According to one aspect, the transducer includes a piezoelectric micromachined ultrasonic transducer (PMUT) disposed to generate the interface modes or the transducer includes a magnetic actuated micromachined ultrasonic transducer disposed to generate the interface modes.

Figure 6:
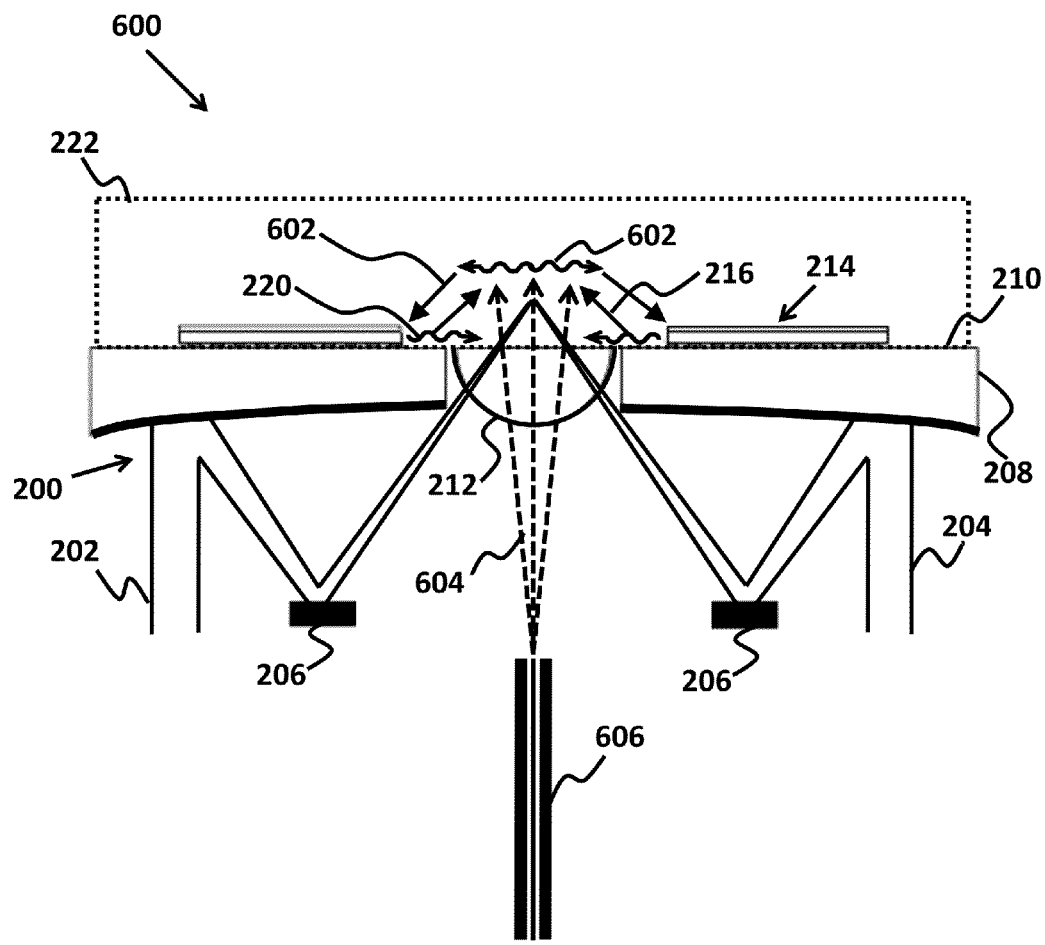
FIG. 6 shows a planar schematic view of an integrated delivery assisting device having photo-acoustic imaging, according to one aspect of the current invention.

FIG. 6 shows an integrated delivery assisting device having photo-acoustic imaging 600, according to the current invention. According to one aspect, the transducer 214 can be bi-static or mono-static, where the bi-static transducer is disposed to transmit and to receive acoustic signals, and the mono-static transducer is disposed to transmit or to receive acoustic signals 602.

In another aspect of the invention, the imaging device 200 can be a focused optical beam 218, or a scanned focused laser beam 604. According to one aspect of the invention, the laser beam 604 can be pulsed or continuous wave (CW).

In one aspect, the pulsed laser beam 604 is disposed to provide energy that is absorbed by a target 222 to induce a thermoelastic expansion in the target 222. The thermoelastic expansion generates interface acoustic waves 602 that propagate laterally from the target region 222. The interface waves 602 are received by a transducer 214 disposed to operate in a receiving mode, where the location of the target 222 is then mapped according the instantaneous location of the scanned focal point. According to the invention, a higher resolution is achieved according to a sharper focal point of the imaging laser 606. In this example, the focus 604 of the laser beam is steered across a plane of the tissue 222 area during pulsed operation to provide a range of signals for mapping the target 222. Here, the target 222 may be isolated using contrast agents, where the transducer output 216 provides enhanced penetration of the dye using ultrasound waves 216.

According to one aspect of the invention, the photo-acoustic imaging and optical imaging are complementary modalities, where the microscope 200 can be disposed to provide reflectance or fluorescence imaging, or the pulsed laser 606 can be disposed to provide photo-acoustic imaging.

In another aspect of the invention, once the target 222 has been mapped, when the probe penetration power is low, the transducer power can be increased to a power sufficient to kill cell tissue in the target 222 for tumor treatment. In one aspect, the transducer 214 can be switched from a receive mode to a transmit mode to detect and then treat the target 222, where the transducer 214 provides an imaging function and a tissue-burning function.

In another aspect of the invention, the laser light 604 can be switched from pulsed to CW or from CW to pulsed using one or more laser light sources.

Because current transducers used for ultrasound assisted drug delivery are bulky and not integrated with other imaging devices. One aspect of the current invention enables a miniaturized device that combines optical, laser or ultrasound imaging with an ultrasound therapeutic device to enhance drug delivery. The SAW-based circular devices are planar and have a natural geometric focal point due to the circular symmetry. Compared to having an array of ultrasound transducers arranged on a plane, the SAW devices of the current invention are much simpler to operate because they require fewer electrical connections than an array.

There are many possible variations and different applications of the general approach. For example, in one aspect the invention can be used to assist the delivery of drugs for therapeutics or just biomarkers to be used as indicators of biological processes. Further, the catheter-based versions of the according to the current invention can be used for thrombolysis which can be applied with or without thrombolytic drugs.

Other variations of the described invention include imaging devices that can be optical, ultrasonic, or any other modality. Further, the therapy can be applied with or without ultrasound contrast agents (e.g., microbubbles). If a number of electrical connections is not a problem for a given application, an annular array of ultrasound transducers can be disposed on a planar surface such as the backside of the mirror in the above example to achieve variable depth of focus.

What is claimed:
1. An ultrasound assisted delivery device, comprising:
   a. a focused ultrasound transducer having an ultrasound focal point;
   b. a real-time optical imaging device comprising an imaging mirror having an optical focal point, wherein said focused ultrasound transducer is disposed on a backside of said imaging mirror, wherein said ultrasound focal point is at a distance that is proximal to $3 \times 10^{-1}$ mm from said imaging mirror backside; and
   c. a therapeutic delivery device, wherein said focused ultrasound transducer and said real-time optical imaging device are integrated with said therapeutic delivery device, wherein said ultrasound focal point coincides with said optical focal point, wherein said therapeutic delivery device and said focused ultrasound transducer are disposed to provide an unobstructed imaging path for said real-time optical imaging device.

2. The ultrasound assisted delivery device of claim 1, wherein said focused ultrasound transducer is selected from the group consisting of piezoelectric material, capacitive micromachined ultrasonic transducers (CMUT) and piezoelectric micromachined ultrasonic transducers (PMUT).

3. The ultrasound assisted delivery device of claim 1, wherein said therapeutic delivery device comprises an endoscope, a catheter providing internal delivery, or an external device providing skin delivery.

4. The ultrasound assisted delivery device of claim 1, wherein said real-time imaging device comprises a dual-axis confocal microscope, wherein said focused ultrasound transducer is disposed on a back side of an imaging mirror in said dual-axis confocal microscope.

5. The ultrasound assisted delivery device of claim 1, wherein said focused ultrasonic transducer comprises a circular pattern of electrodes.

6. The ultrasound assisted delivery device of claim 5, wherein said focused ultrasonic transducer provides a radial pattern of surface acoustic waves, or Lamb waves on a surface of a target for delivery, wherein said radial pattern of surface acoustic waves or said Lamb waves undergo a mode conversion to longitudinal waves to provide a focused ultrasonic beam.

7. The ultrasound assisted delivery device of claim 1, wherein said focused ultrasonic transducer is an interdigital ultrasonic transducer comprising a piezoelectric material, a first interdigital electrode, a second interdigital electrode and a metal layer, wherein said first interdigital electrode is disposed on a back side of an imaging mirror in said real-time imaging device and said second interdigital electrode is disposed proximal to said first electrode, wherein said piezoelectric material is disposed on said first electrode and on said second electrode, wherein said metal layer is disposed on said piezoelectric material.

8. The ultrasound assisted delivery device of claim 7, wherein a spacing between said first electrode and said second electrode is about one quarter wavelength of a leaky Rayleigh wave.

9. The ultrasound assisted delivery device of claim 1, wherein said focused ultrasonic transducer is an edge bonded ultrasonic transducer comprising a piezoelectric material, a first segmented cylindrical electrode and a second segmented cylindrical electrode, wherein said first segmented cylindrical electrode is disposed about an edge of an said imaging mirror in said real-time imaging device, wherein said piezoelectric material is disposed on said first segmented electrode, wherein said second segmented cylindrical electrode is disposed on said piezoelectric material, wherein said piezoelectric material is electrically driven to generate surface acoustic waves along a back surface of said imaging mirror.

10. The ultrasound assisted delivery device of claim 1, wherein said focused ultrasonic transducer comprises a spherically focused ultrasonic transducer comprising a parabolic first electrode, a piezoelectric material disposed on said parabolic first electrode and a second electrode disposed on said piezoelectric material.

11. The ultrasound assisted delivery device of claim 1 further comprising a laser beam, wherein said laser beam comprising a laser beam focal point, wherein said therapeutic delivery device is disposed to deliver an optical contrast material to said target, wherein said laser beam focal point coincides with said ultrasound focal point and with said optical focal point, wherein said laser beam focal point is disposed to sweep across said target, wherein said target or said optical contrast material absorbs energy from said laser beam focal point to generate at least one interface acoustic wave.

12. The ultrasound assisted delivery device of claim 11, wherein said focused ultrasound transducer comprises a bi-static transducer or a mono-static transducer, wherein said bi-static transducer is disposed to transmit and to receive acoustic signals, wherein said mono-static transducer is disposed to receive said acoustic signals.

13. The ultrasound assisted delivery device of claim 11, wherein said at least one interface signal comprises i) a fluorescence signal formed by said contrast material absorbing energy from said laser focal point, ii) interface acoustic waves formed by endogenous absorption in said target, iii) interface acoustic waves formed by exogenous absorbing contrast agents in said target, i) and ii), ii and iii), or i) and iii), wherein said fluorescence signal is received by said real-time imaging device, wherein said interface acoustic waves are laterally propagating waves that are received by said transducer, wherein said transducer is disposed to operate in a receiving mode.

14. The ultrasound assisted delivery device of claim 11, wherein said laser light source comprises i) a pulsed laser light source. ii) a continuous wave laser light source, or i) and ii).

15. The ultrasound assisted delivery device of claim 1, wherein said transducer can be switched from a receive mode to a transmit mode, wherein when in said receive mode said transducer is disposed for imaging said target and when in said transmit mode said transducer is disposed to enhance ultrasound penetration for a contrast agent or enhance therapeutic agent penetration for treating said target.

16. The ultrasound assisted delivery device of claim 11, wherein an output power of said transducer is adjustable.

17. The ultrasound assisted delivery device of claim 11, wherein said optical contrast material is selected from the group consisting of lipid nanoparticles, metallic nanoparticles, and fluorescent dye.

18. An ultrasound assisted delivery device, comprising:
a. a transducer, wherein said transducer comprises capacitive micromachined ultrasonic transducers (CMUT) arranged in an interdigital pattern capable of providing interface modes;
b. an optical imaging device comprising an imaging mirror having an optical focal point, wherein said transducer is disposed on a backside of said imaging mirror, wherein said transducer comprises an ultrasound focal point at a distance that is proximal to $3 \times 10^{-1}$ mm from said imaging mirror backside; and
c. a therapy delivery device, wherein said transducer and said optical imaging device are integrated with said therapeutic delivery device, wherein said interface modes are disposed to focus at a center of said transducer and disposed to coincide with said optical focal point and said delivery focus point, wherein said therapeutic delivery device and said focused ultrasound transducer are disposed to provide an unobstructed imaging path for said optical imaging device.

19. The ultrasound assisted delivery device of claim 18, wherein said transducer comprises a piezoelectric micromachined ultrasonic transducer (PMUT) disposed to generate said interface modes.

20. The ultrasound assisted delivery device of claim 18, wherein said transducer comprises a magnetic actuated micromachined ultrasonic transducer disposed to generate said interface modes.

* * * * *